United States Patent [19]

Sugg

[11] Patent Number: 4,867,158

[45] Date of Patent: Sep. 19, 1989

[54] HAND HELD BATTERY POWERED BONE AWL

[76] Inventor: Winfred L. Sugg, 4209 San Carlos, Dallas, Tex. 75205

[21] Appl. No.: 75,648

[22] Filed: Jul. 20, 1987

[51] Int. Cl.$^4$ ............................................. A61B 17/32
[52] U.S. Cl. ................................. 128/305.1; 128/92 V
[58] Field of Search .......... 128/305, 312, 313, 92 VD, 128/92 V, 305.1, 310, 92 VJ; 30/362, 272 A; 408/6, 124; 409/181, 182, 134; 173/163, 15, 170; 310/47, 50

[56] References Cited

U.S. PATENT DOCUMENTS

| | | | |
|---|---|---|---|
| 1,308,798 | 7/1919 | Masland | 128/92 VD |
| 1,543,847 | 6/1925 | Heidbrink | 128/305 |
| 2,525,669 | 10/1950 | Hainault | 128/310 |
| 3,109,238 | 11/1963 | Marks | 173/163 |
| 3,173,417 | 3/1965 | Horner | 128/305.1 |
| 3,343,192 | 9/1967 | Goldstein et al. | 310/50 |
| 3,682,177 | 8/1972 | Ames et al. | 128/310 |
| 3,734,207 | 5/1973 | Fishbein | 173/163 |
| 3,935,909 | 2/1976 | Mabuchi et al. | 408/124 |
| 4,522,270 | 6/1985 | Kishi | 173/163 |

FOREIGN PATENT DOCUMENTS 1381387 1/1975 United Kingdom ................ 173/163

OTHER PUBLICATIONS

Skil Corporation advertisement–Cordless Power Screwdriver–Jun. 1986.

Primary Examiner—Andrew M. Dolinar
Attorney, Agent, or Firm—Richards, Harris, Medlock & Andrews

[57] ABSTRACT

A hand held, self powered bone awl (10, 50) is disclosed which can be held in the hand of a surgeon for drilling holes through bone, such as the sternum bone during open heart surgery. In one embodiment, the awl is activated by a finger operated switch (38). In another embodiment, a pressure activated switch (52) operates the awl when the end of the bone awl bit (20) is pushed against the bone to be drilled. In either embodiment, a predetermined length (24) of the bit (20) is exposed to limit the depth of drilling to prevent damage to tissue behind the bone.

8 Claims, 1 Drawing Sheet

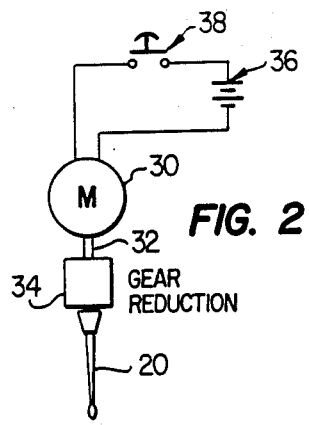
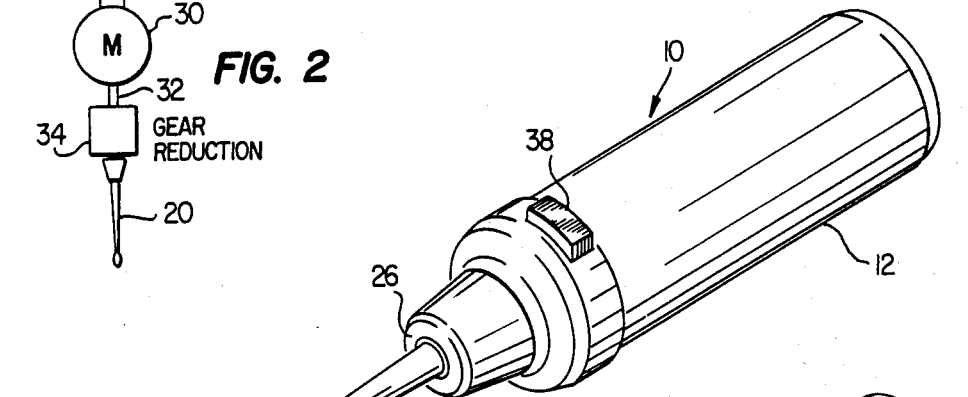
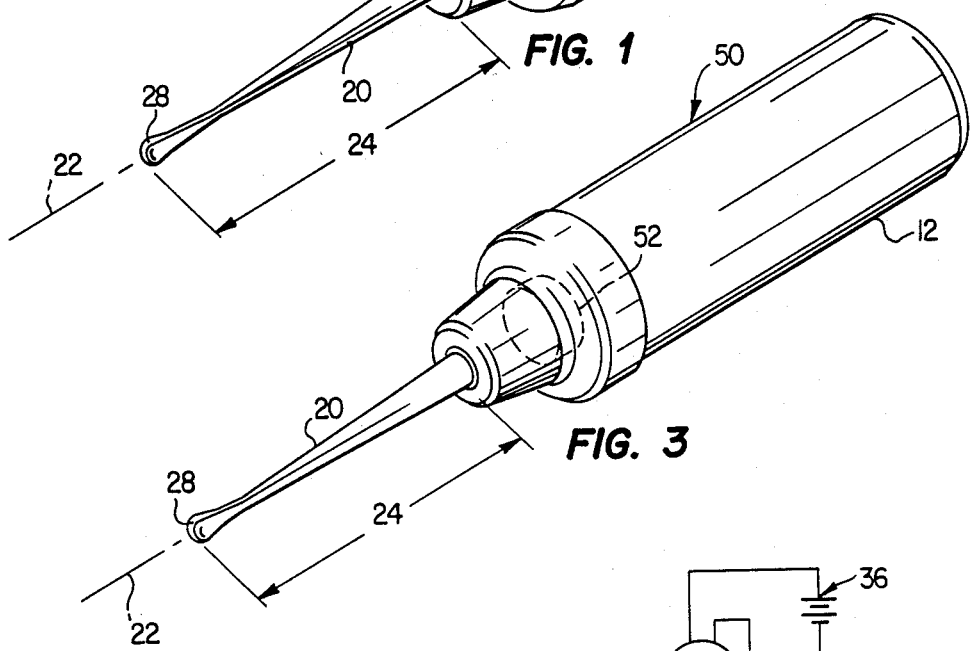
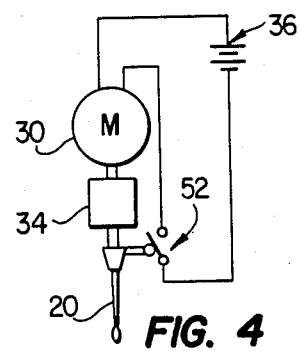

HAND HELD BATTERY POWERED BONE AWL

TECHNICAL FIELD

This invention relates to the medical field, and particularly to open heart surgery.

BACKGROUND OF THE INVENTION

In open heart surgery, it is necessary to split the sternum bone along the body's plane of symmetry to separate the ribcage and gain access to the heart. After surgery, the two halves of the sternum bone must be rejoined and stabilized, permitting the bones to knit together during the recovery process.

To knit properly, the two halves of the sternum bone must be physically tied together. Commonly, the surgeon drills a series of about ten holes through one half of the sternum bone and a similar set of ten holes in the other half of the sternum bone which allows a tie to be laced between adjacent holes in each half to tie the halves together.

The holes are now made by a bone awl, which includes a bone awl bit and a handle. The surgeon grasps the awl by the handle and manually drills the hole by rotating the awl while forcing the awl against the sternum bone. This procedure takes considerable time, lengthening the exposure of the patient to the trauma of surgery, and also is physically exhausting to the surgeon. A need thus exists for an improved apparatus or method for providing the necessary holes needed for stabilization of the sternum bone halves to permit knitting.

SUMMARY OF THE INVENTION

A bone awl is provided which includes a casing for grasping in the hand of a surgeon. An enlongate bone awl bit is provided which is capable of drilling through bone when rotated about its longitudinal axis. Structure in the casing mounts the enlongate bone awl bit to the casing for rotation about its longitudinal axis with a predetermined length of the bone awl bit extending outward from a first end of the casing. A motor is mounted within the casing for rotating the bone awl bit about its longitudinal axis. A power source is mounted within the casing for providing power to operate the motor. Switch structure is mounted proximate the first end of the casing for activation by the finger of the surgeon to connect the power source to the motor to rotate the bone awl bit. The exposed predetermined length of the bit is selected to drill through the bone, while preventing the bit from penetrating tissue behind the bone.

In accordance with another aspect of the present invention, the power source can be replenished, either by replacing the power source or reenergizing the power source.

In an alternate embodiment, the finger activated switch structure can be replaced by switch structure which is activated by pressing the tip of the bit against the bone being drilled.

BRIEF DESCRIPTION OF THE DRAWINGS

For a more complete understanding of the present invention and the advantages thereof, reference is now made to the following description taken in conjunction with accompanying drawings, of which:

FIG. 1 is a perspective view of a hand held, self powered bone awl forming a first embodiment of the present invention;

FIG. 2 is an electrical schematic of the circuit within the bone awl of FIG. 1;

FIG. 3 is a perspective view of a second embodiment of a hand held, self-powered bone awl;

FIG. 4 is an electrical schematic of the circuit within the bone awl of FIG. 2.

DETAILED DESCRIPTION

Referring now to FIGS. 1 and 2, a first embodiment of the present invention is illustrated as hand held, self powered bone awl 10. The awl includes a casing 12 which is especially adapted to be grasped by the hand of the surgeon. The shape should allow the surgeon to firmly grasp the awl 10 and direct its usage to drill the required holes through bone, typically the sternum bone.

A bone awl bit 20 is mounted to the casing 12 for rotational motion about its enlongate axis 22. A predetermined length 24 of the bit 20 extends exterior the casing 12 at the first end 26 of the casing 12. The bone awl bit 20 has an end 28 with suitably configured cutting elements to drill through the bone with minimum force applied along the longitudinal axis 22 when the bit is rotated about the axis 22.

Also mounted within the casing 20 is an electric motor 30 with a rotating drive shaft 32. The motor 30 is mounted so that the drive shaft 32 rotates about axis 22 as well. A gear reduction coupling 34 connects the drive shaft 32 with bit 20. Alternatively, the bit 20 can form part of the drive shaft 32, if desired.

A battery 36 is also mounted within the casing 12 and connected electrically with the motor 30 through a finger activated switch 38 mounted in the casing 12 proximate the first end 26. The hand of the surgeon holding the awl 10 will be holding the awl so that the index finger can readily push the switch 38 to connect the battery 36 to electric motor 30 to spin the drive shaft 32, and bit 20, in a first direction about the axis 22. The surgeon can then drill a hole holding end 28 of the bit 20 against the bone until the hole is drilled.

The predetermined length 24 of bit 20 external the casing 12 is precisely set so that the first end 26 of the casing 12 will contact the bone just as the hole is completed to prevent further incursion of the bit into tissue behind the bone. The battery 36 preferably has sufficient energy to drill sufficient holes to finish at least one complete surgical procedure. The battery 36 can be of the replaceable type, or the rechargeable type, wherein the battery is recharged between surgical procedures.

With reference now to FIG. 3 and 4, a hand held, self powered bone awl 50 is disclosed which forms a second embodiment of the present invention. Awl 50 has a pressure activated switch 52 which provides power from the battery 36 to the motor 30 when the end 28 of bit 20 is pushed with sufficient force against the bone to be drilled. Thus, the finger actuated switch 38 is eliminated to further facilitate use by the surgeon. The pressure activated switch 52 has the further advantage as it can be set to rotate the awl only when pressed against a hard surface such as bone. Pressing the tip of the bit against tissue behind the bone would not provide sufficient pressure to activate the switch and the switch thus acts as a backup to the set length 24 to avoid tissue damage.

While several embodiments of the invention have been illustrated in the accompanying drawings and described in the foregoing detailed description, it will be understood that the invention is not limited to the embodiments disclosed, but is capable if numerous rearrangements, modifications and substitutions of parts and elements without parting from the scope and spirit of the invention.

I claim:

1. A bone awl for drilling an aperture in the sternum bone to tie together the sternum bone after open heart surgery with a tie, comprising:

a casing for grasping in the hand of a surgeon;

an elongate bone awl bit for rotation about a longitudinal axis thereof to drill through bone, the elongate bone awl bit for drilling an aperture in the sternum bone to accept the tie;

means for mounting the bit to the casing for rotation about the longitudinal axis of the bit, a predetermined length of the bit extending outward from the casing at a first end of the casing, the casing preventing the bone awl bit from penetrating through the sternum bone and into the underlying tissue beyond the predetermined length;

motor means mounted within the casing for rotating the bit about its longitudinal axis;

a power source mounted within the casing for operating said motor means;

switch means mounted to the casing to connect the power source to said motor means to rotate the bit for drilling.

2. The bone awl of claim 1 wherein said switch means is a finger activated switch mounted proximate the first end of the casing.

3. The bone awl of claim 1 wherein said switch means is a pressure activated switch activated by pressing the end of the bit against the bone to be drilled.

4. The bone awl of claim 1 wherein the exposed predetermined length of bit prevents the bit from cutting into tissue behind the bone being drilled.

5. The bone awl of claim 1 wherein the power source is replaceable.

6. The bone awl of claim 1 wherein the power source is rechargeable.

7. A bone awl for drilling holes through the separated sections of the sternum bone after open heart surgery to tie the sections of the sternum bone together, comprising:

a casing for grasping in the hand of a surgeon;

an elongate bone awl bit for rotation about its longitudinal axis to drill through the sternum bone to drill a hole to receive the tie;

means for mounting the bit to the casing for rotation about the longitudinal axis of the bit, a predetermined length of the bit extending outward from the casing proximate a first end thereof, the casing preventing the bone awl bit from penetrating through the sternum bone and into underlying tissue beyond a distance corresponding to the predetermined length to prevent injury to the patient;

a motor mounted within the casing for rotating the bit rotating its longitudinal axis;

a power source mounted within the casing for operating said motor; and a finger activated switch mounted to the casing proximate the first end for selectively connecting the power source to the motor to rotate the bit for drilling.

8. A bone awl for drilling holes in separated sections of the sternum bone after open heart surgery to receive a tie to hold the sections together for knitting, comprising:

a casing for grasping in the hand of a surgeon;

an elongate bone awl bit for rotation about its longitudinal axis for drilling through bone, the bone awl bit for drilling a hole in the sternum bone section to receive the tie;

means for mounting the bit to the casing for rotation about the longitudinal axis of the bit, a predetermined length of the bit extending outward from the casing proximate a first end of the casing, the first end of the casing contacting the section of the sternum bone being drilling as a hole is drilled to prevent penetration of the bone awl bit through the sternum bone section and underlying tissue beyond a depth corresponding to the predetermined length of the bit to prevent injury to the patient;

a motor mounted within the casing for rotating the bit about its longitudinal axis;

a power source mounted within the casing for operating the motor; and a pressure activated switch mounted on the casing for connecting the power source to the motor when the drill bit is forced against bone to be drilled.

* * * * *